United States Patent [19]
Rapacki et al.

[11] Patent Number: 5,569,274
[45] Date of Patent: Oct. 29, 1996

[54] ENDOSCOPIC VASCULAR CLAMPING SYSTEM AND METHOD

[75] Inventors: Alan R. Rapacki, San Francisco; John H. Stevens, Palo Alto, both of Calif.

[73] Assignee: Heartport, Inc., Redwood City, Calif.

[21] Appl. No.: 265,477

[22] Filed: Jun. 24, 1994

Related U.S. Application Data

[63] Continuation-in-part of Ser. No. 23,778, Feb. 22, 1993, Pat. No. 5,452,733.

[51] Int. Cl.⁶ .................................................. A61B 17/00
[52] U.S. Cl. ........................ 606/158; 606/142; 606/151; 227/901; 227/902; 128/898
[58] Field of Search ................................ 606/142, 143, 606/139, 151, 157, 158, 221; 227/901, 902; 128/843, 898

[56] References Cited

U.S. PATENT DOCUMENTS

| | | | |
|---|---|---|---|
| 3,506,012 | 4/1970 | Brown | 606/142 |
| 3,877,434 | 4/1975 | Ferguson et al. . | |
| 3,958,576 | 5/1976 | Komiya | 606/142 |
| 4,174,715 | 11/1979 | Hasson . | |
| 4,241,734 | 12/1980 | Kandel et al. | 606/142 |
| 4,269,190 | 5/1981 | Behney | 606/157 |
| 4,367,746 | 1/1983 | Derexhinsky | 606/142 |
| 4,374,523 | 2/1983 | Yoon . | |
| 4,660,558 | 4/1987 | Kees, Jr. | 606/158 |
| 4,681,107 | 7/1987 | Kees, Jr. . | |
| 4,706,668 | 11/1987 | Backer . | |
| 4,777,949 | 10/1988 | Perlin . | |
| 4,932,955 | 6/1990 | Merz et al. . | |
| 4,961,743 | 10/1990 | Kees, Jr. et al. | 606/158 |
| 5,059,202 | 10/1991 | Liang et al. . | |
| 5,074,870 | 12/1991 | Von Zeppelin . | |
| 5,242,456 | 9/1993 | Nash et al. | 606/142 |
| 5,304,183 | 4/1994 | Grourlay et al. | 606/151 |
| 5,368,600 | 11/1994 | Faila et al. . | |

FOREIGN PATENT DOCUMENTS

| | | |
|---|---|---|
| WO93/09721 | 5/1993 | WIPO . |
| WO93/18712 | 9/1993 | WIPO . |

*Primary Examiner*—Michael Powell Buiz
*Assistant Examiner*—Jeffrey A. Schmidt
*Attorney, Agent, or Firm*—Townsend and Townsend and Crew LLP

[57] ABSTRACT

The invention provides a system and method for performing less-invasive surgical procedures within a body cavity. In a preferred embodiment, the invention provides a system and method for temporarily occluding a blood vessel in an arterial graft in a thoracoscopic coronary artery bypass grafting procedure. The system comprises a clamp (2) and an introducer (1) for introducing the clamp through a percutaneous penetration into the body cavity and applying the clamp to a tissue structure such as a blood vessel. The clamp has a pair of movable jaws (65, 67) coupled to one another, each jaw having a distal portion for engaging the tissue structure and a proximal portion having a camming surface (66, 68). The introducer has a longitudinal shaft (3) with a clamp engaging member (25) slidably coupled to the distal end of the shaft for releasably holding the clamp. A handle (11) is coupled to the proximal end of the shaft. The handle can be manipulated to axially slide the shaft with respect to the clamp engaging member so that the shaft engages the camming surfaces of the clamp to open and close the distal portions of the jaws without releasing the clamp from the introducer.

48 Claims, 12 Drawing Sheets

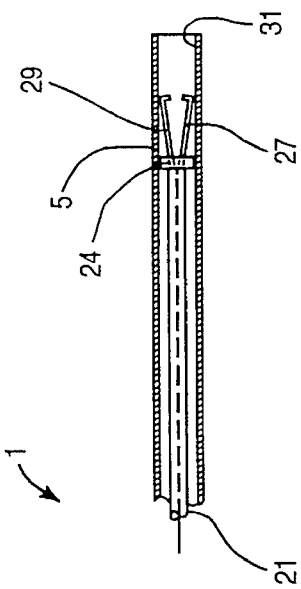
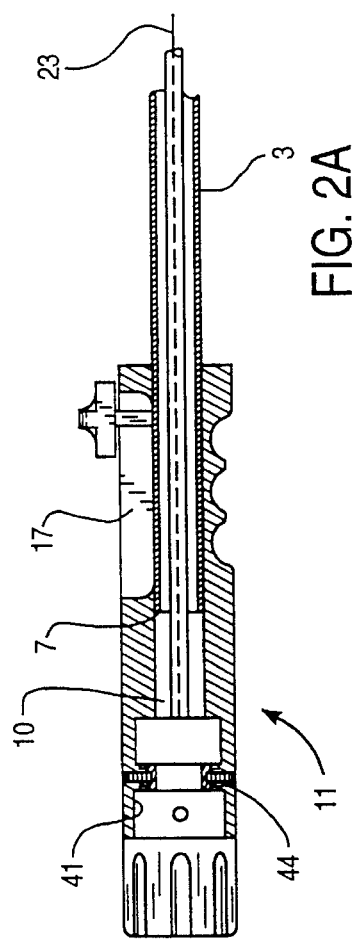
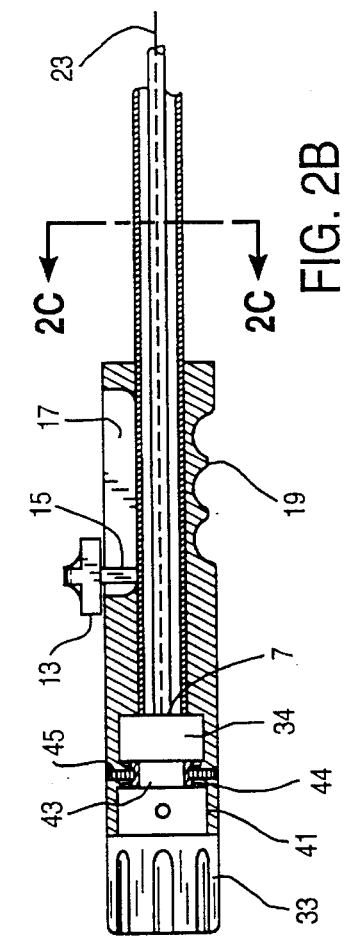
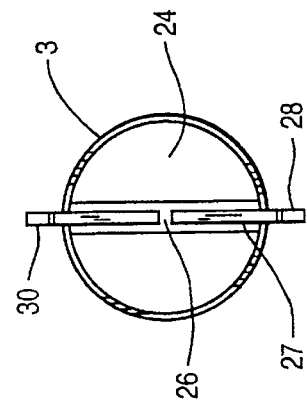

ns, a vascular
ENDOSCOPIC VASCULAR CLAMPING SYSTEM AND METHOD

CROSS-REFERENCE TO RELATED APPLICATIONS

This application is a continuation-in-part of application Ser. No. 08/023,778, filed Feb. 22, 1993, now U.S. Pat. No. 5,452,733 the complete disclosure of which is incorporated herein by reference.

FIELD OF THE INVENTION

This invention relates generally to a system and method for performing less-invasive surgical procedures, and more specifically, to a system and method for temporarily occluding a blood vessel in a thoracoscopic coronary artery bypass grafting procedure.

BACKGROUND OF THE INVENTION

In coronary artery disease, the build-up of artherosclerotic plaque on the inner walls of the coronary arteries causes a narrowing or complete closure of these arteries, resulting in insufficient blood flow to the heart. This condition has become one of the most common life-threatening medical problems facing older men and women.

A number of approaches have been developed for treating coronary artery disease. In less severe cases, it is often sufficient to treat the symptoms with pharmaceuticals and lifestyle modification to lessen the underlying causes of the disease. In more severe cases, a coronary artery blockage can often be treated using endovascular techniques such as balloon angioplasty, atherectomy, laser or hot tip ablation, placement of stents, and the like.

In cases where pharmaceutical treatment and/or endovascular approaches have failed or am likely to fail, it is often necessary to perform a coronary artery bypass graft procedure using open surgical methods. Such methods require that the patient's sternum be divided longitudinally and the chest be spread apart to provide access to the heart, an access technique known as a median sternotomy. While the patient's heart is arrested using cardioplegic agents and the patient is supported by cardiopulmonary bypass, a vascular source of arterial blood is then connected to a coronary artery downstream from the blockage. The arterial blood source may be a venous or arterial graft vessel connected between an arterial source such as the aorta and the coronary artery. Another common arterial blood source is the left or right internal mammary artery which may be grafted to the coronary artery which is narrowed or occluded. Recent studies have suggested that the use of mammary arteries as an arterial blood source may be advantageous over other sources due to a greater likelihood that the graft will remain patent over time.

In order to use a mammary arterial graft in a coronary artery bypass procedure, blood flow through the target mammary artery must be temporarily stopped. For this purpose, a removable surgical clamp is applied to the mammary artery at a position downstream from the patient's aorta. In a conventional open-chest procedure, a relatively large, easy to handle clamp is used which can be applied by hand or with a forcep directly to the mammary artery through the large opening in the patient's chest provided by a median sternotomy. After the mammary artery is clamped, it is ligated and divided at a location downstream from the clamp to create a free end which may be connected to the coronary artery. After the grafting is complete, the clamp is removed by the surgeon, again typically by hand or with the open forceps, to permit blood to flow through the mammary artery and into the coronary artery downstream of the blockage.

While very effective in many cases, conventional open heart surgical techniques of coronary artery bypass grafting are highly traumatic to the patient due to the necessity of a median sternotomy or other form of gross thoracotomy. Therefore, new methods of performing surgery on the heart using minimally-invasive techniques have been recently developed. In these methods, the patient's heart is arrested by occluding the patient's aorta between the coronary arteries and the brachiocephalic artery with an expandable balloon on the distal end of an endovascular catheter introduced via a femoral artery. Cardioplegic fluid is then delivered to the patient's myocardium through a lumen in the same catheter or through a separate catheter positioned in the coronary sinus. This method allows the surgeon to perform operations such as coronary artery bypass grafting without creating a large opening in the patient's chest. Minimally-invasive cutting and suturing instruments can be introduced thoracoscopically to isolate and dissect a mammary artery and to connect the free end of the mammary artery to an incision in the coronary artery. A complete description of such methods is found in commonly assigned, co-pending application Ser. No. 08/023,778, filed Feb. 22, 1993 now U.S. Pat. No. 5,456,733 which has been incorporated herein by reference.

This new generation of thoracoscopic methods of performing coronary artery bypass grafting has, of course, created many new challenges. One such challenge arises from the inability to clamp the mammary artery by manually applying a surgical clamp through the large opening in the patient's chest. Instead, the clamp must be introduced in a minimally-invasive manner through a small percutaneous incision or cannula positioned in an intercostal space in the patient's rib cage.

It is known in certain surgical procedures, especially laparoscopic procedures, to use long-handled introducers for applying clamps to internal tissue within a body cavity such as the abdomen. These introducers typically include a pair of movable jaws or arms for holding a clamp at the distal end of an elongated shaft. The clamp is placed in the arms of the introducer and the distal end of the introducer is introduced through a trocar sleeve into the body cavity. The clamp is then positioned at the desired tissue location and an actuator on the proximal end of the introducer is actuated to apply the clamp to the tissue. Examples of such systems are seen in U.S. Pat. No. 4,174,715 to Hasson, PCT Application No. PCT/US93/02670 to Gourlay (Publication No. WO 93/18712) and PCT Application No. PCT/US92/06186 to Kensey (Publication No. WO 93/09721).

These known devices, however, suffer from a number of disadvantages. Known introducers typically hold onto the clamp with the same mechanism (e.g. a pair of arms) that allows the clamp to close onto the tissue. Therefore, the jaws of the clamp cannot be allowed to close onto the tissue without releasing the clamp from the arms of the introducer. After the clamp has been applied (and thus released from the introducer), the surgeon cannot manipulate the clamp and the tissue to which it is attached by manipulating the introducer. In addition, it may be necessary to reapply the clamp if the first attempt did not completely occlude the blood vessel or if the clamp was improperly positioned. Thus, the surgeon must relocate the clamp and engage it with the introducer to open the jaws and reposition the clamp.

This is particularly difficult in minimally invasive procedures in which visualization and access is limited.

Another disadvantage of known introducers is that the clamp is typically held by the introducer at multiple engagement points. For example, the device disclosed in the Gourlay application closes two arms on the distal end of the introducer onto two handles on the proximal end of the clamp to grasp the clamp. This approach makes it very difficult to re-engage the clamp because the surgeon must line up the arms of the introducer with both handles of the clamp. This further limits the angle in which the clamp may be approached and re-engaged by the introducer arms.

Further, known clamps and introducers are not well-suited for occluding a mammary artery in coronary artery bypass grafting procedures. For example, blood flows through the mammary artery at a higher pressure (typically 70–100 mm of mercury) than the pressure in other fluid conducting ducts to which such clamps are typically applied. Known clamps that can be introduced through a percutaneous incision in the body generally do not provide sufficient clamping force to occlude the mammary artery. Moreover, the clamps and forceps used for arterial clamping in open-chest surgery are typically adapted for manual insertion through a gross thoracotomy and are usually too large to be introduced through a small percutaneous, intercostal incision or cannula.

For these and other reasons, improved systems and methods are desired for clamping fluid-carrying vessels in a body cavity via a small percutaneous incision or cannula. Preferably, the system would be capable of temporarily occluding a mammary artery during a coronary artery bypass grafting procedure. The system should allow the surgeon to apply the clamp onto the mammary artery without releasing the clamp from the introducer so that the clamp may be repositioned without having to relocate the clamp. The system should also allow the clamp to be engaged and opened at a single point. In addition, the system should be configured for delivery through a percutaneous intercostal incision and the clamp should have sufficient closing force to completely occlude the mammary artery without damaging the vessel under blood flow pressures of 100 mm Hg or greater.

SUMMARY OF THE INVENTION

The present invention provides a system and method for temporarily clamping a tissue structure such as a blood vessel through a small percutaneous penetration in a patient. The invention allows the surgeon to apply a clamp to the tissue structure using a minimally-invasive introducer. The introducer can apply the clamp without releasing it so that the tissue structure can be repositioned by manipulating the introducer, or the clamp can be easily reopened and repositioned on the structure without releasing it from the introducer. The introducer grasps and releases the clamp at a single point so that the clamp can be easily engaged from a variety of directions. The clamp is particularly well suited for occluding high pressure arteries such as the mammary arteries, making the invention particularly useful for temporarily clamping such arteries during surgeries such as coronary artery bypass grafting. While being especially suited for thoracoscopy, the system and method of the invention are also useful in other surgical procedures, such as laparoscopy, pelviscopy, endoscopy and arthroscopy.

In one aspect of the invention, the system comprises a clamp having a pair of movable jaws coupled to one another, each jaw having a distal portion for engaging the tissue structure and a proximal portion having a camming surface. An introducer has a longitudinal shaft with a distal end configured to deliver the clamp through a small percutaneous incision into the body cavity. A means for releasably connecting the clamp to the introducer is slidably coupled to the distal end of the shaft. The introducer further includes actuator means for axially sliding the shaft with respect to the connecting means so that the shaft engages the camming surfaces of the clamp to open and close the distal portions of the jaws.

In a preferred embodiment, a biasing means is provided to exert a spring force that biases the jaws into a closed position. In this embodiment, the camming surfaces are oriented at an acute angle with respect to the axial direction so that these surfaces flare outward in the distal direction. With this configuration, the shaft may be moved in an axial direction so that a channel in the shaft engages the camming surfaces and slides along them to force the proximal portions of the jaws towards each other, thereby opening the distal portions of the jaws. When the shaft is moved in the opposite direction, the biasing means urges the proximal portions apart thereby closing the distal portions of the jaws.

In a preferred embodiment, the connecting means is configured to engage the clamp at a single point. This permits engagement from a variety of different directions and angles to facilitate re-engagement of the clamp after it has been released from the introducer.

In one embodiment, the clamp has a transverse bore or eyelet through or attached to each jaw and the connecting means comprises an engaging means slidably mounted within the shaft for engaging the bore or eyelet. The engaging means preferably comprises a pair of opposing arms biased radially outward so that axial movement of the shaft with respect to the arms opens and closes the arms. The arms have distal tips adapted to seat within the bore on the clamp when closed by axial translation of the shaft. As the shaft moves distally relative to the clamp, the distal tips of the arms will preferably seat within the bore of the clamp before the shaft engages the camming surfaces. Thus, the distal portions of the jaws can be opened and closed without releasing the clamp from the applicator.

In a second embodiment, the engaging means comprises a hook slidably mounted to the distal end of the shaft. The introducer is manipulated by the surgeon so that the hook slides into the transverse bore or eyelet to hold the clamp. The hook may then be drawn into the axial passage in the shaft to secure and/or open the clamp. In a third embodiment, the connecting means comprises a pair of jaws defining a socket configured to receive a ball-shaped handle on the proximal end of the clamp. The jaws are slidably disposed in the axial passage of the shaft and are biased outward so that axial movement of the shaft with respect to the jaws opens and closes the jaws.

The above embodiments allow the surgeon to open and close the jaws of the clamp without releasing the clamp from the introducer. Thus, the surgeon may easily reposition the clamp on the blood vessel without having to relocate the clamp and re-engage it with the introducer (e.g. if the blood vessel has not been sufficiently occluded). In addition, the blood vessel may be repositioned or retracted by manipulating the introducer for improved visualization or access.

To help the surgeon relocate the clamp after it has been released from the introducer, the system includes means for retrieving the clamp. The retrieving means is preferably a flexible tether attached to the jaws of the clamp which may be extended out of the body cavity through a percutaneous incision. If the surgeon loses track of the clamp during the operation, the tether is tensioned to locate the clamp. The tether may also be tensioned to retract or reposition the vessel to which the clamp is attached.

The invention is particularly useful for occluding an artery such as an internal mammary artery during a cardiac procedure such as coronary artery bypass grafting. In this procedure, a cannula is positioned in a percutaneous intercostal penetration on a lateral side of the patient's chest. A viewing scope, such as a thoracoscope or a direct visualization device, is introduced through another percutaneous intercostal penetration. The clamp, releasably connected to the introducer, is then guided through the cannula and positioned with the distal portion of the jaws around the target location of the mammary artery. After positioning the clamp, the shaft of the introducer is moved in a proximal direction with respect to the clamp to release the camming surfaces so that the jaws close onto the mammary artery.

After the jaws have effectively occluded the mammary artery, the shaft is moved further in the proximal direction to release the arms from the bore of the clamp. Once the clamp is released from the introducer, the introducer may be withdrawn from the patient. The tether remains coupled to the clamp and extends out of the body cavity through a percutaneous intercostal penetration or cannula. The mammary artery is then ligated and divided at a location downstream from the clamp to create a free end. The clamp prevents blood from flowing out of the free end. The free end is then connected to the coronary artery downstream of the narrowed or occluded portion of the artery. Finally, the introducer is reintroduced through the cannula to engage the clamp and open the jaws, allowing blood to flow through the mammary artery to the coronary artery. Both the introducer and clamp may then be withdrawn from the patient.

In a preferred embodiment, the jaws of the clamp are formed of a single, continuous length of wire or two lengths of wire riveted together. This configuration is inexpensive, relatively easy to manufacture and the wire provides a small cross-sectional profile to facilitate guiding the clamp through a patient's body. The wire also forms a torsion spring that creates a strong closing force on the distal portion of the jaws sufficient to occlude the mammary artery against the high pressure of blood flow through it. To reduce the risk of damaging the mammary artery under this strong spring force, a soft elastomeric material is preferably placed over the inner surface of the distal portion of the jaws.

It should be understood that while the invention is described in the context of thoracoscopic surgery on the mammary and coronary arteries, the system and method disclosed herein are equally useful on other types of body structures in the abdomen, pelvis, thorax and other body cavities.

A further understanding of the nature and advantages of the invention may be realized by reference to the remaining portions of the specification and the drawings.

BRIEF DESCRIPTION OF THE DRAWINGS

FIGS. 2A–2B are side cross-sectional views of an introducer in the endoscopic clamping system of FIG. 1, illustrating a pair of arms of the introducer in closed and open positions, respectively;

FIGS. 2C is a transverse cross-sectional view of the introducer of FIGS. 2A and 2B;

FIG. 2D is an end view of the distal end of the introducer of FIGS. 2A and 2B;

DETAILED DESCRIPTION OF SPECIFIC EMBODIMENTS

Figure 1:
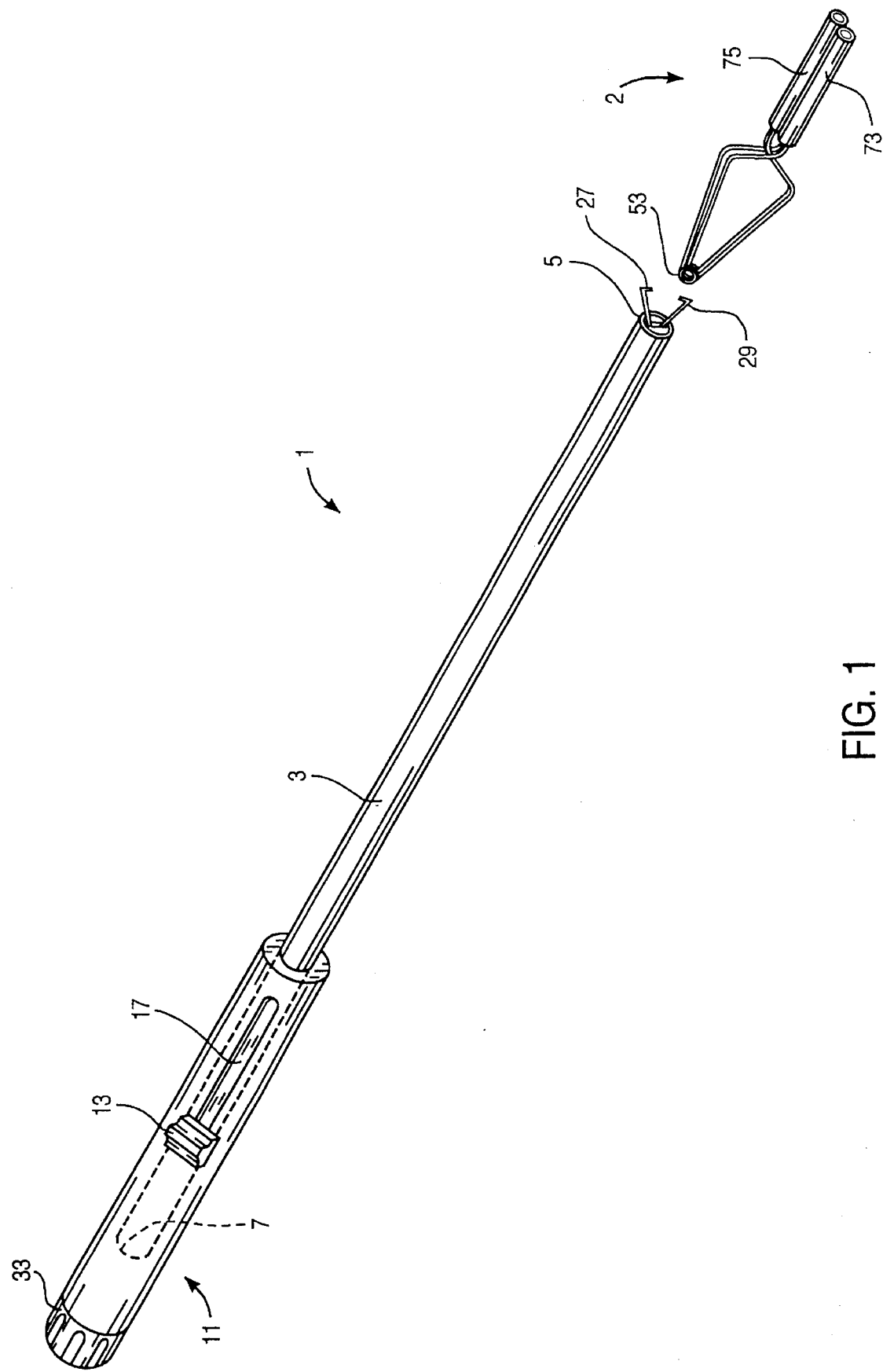
FIG. 1 is a perspective view of a endoscopic clamping system according to the present invention.

The system and method of the present invention for occluding a tissue structure such as a blood vessel will now be described in detail. Referring to FIG. 1, a vascular clamping system according to the invention includes an introducer 1 and a clamp 2 adapted to be releasably held by introducer 1. Introducer 1 includes a shaft 3 having a distal end 5 and a proximal end 7. Shaft 3 is preferably a stainless steel tube having an outer diameter in the range of 3–12 mm, usually 5–10 mm, so as to fit within a cannula having an internal diameter in the range of 4–15 mm. Shaft 3 can also be introduced directly through a percutaneous incision in the patient. Shaft 3 has a length selected to reach a target site in a body cavity, such as the heart, and to extend sufficiently out of the body cavity to facilitate easy manipulation of introducer 1. Thus, shaft 3 should have a length of 10–40 cm and preferably 17–30 cm. It should be noted that although shaft 3 is shown as having a circular cross-sectional shape in the drawings, shaft 3 could have a rectangular, oval, channel or other cross-sectional shape.

Referring to FIGS. 2A–2D, shaft 3 has an axial passage 9 extending from distal end 5 to proximal end 7. Proximal end 7 of shaft 3 is slidably disposed in an axial bore 10 in a handle 11. An actuator button 13 has a lower arm 15 projecting into a longitudinal slot 17 in handle 11. Lower arm 15 of button 13 is axially movable within longitudinal slot 17 and fixed to shaft 3 so that shaft 3 may slide together with button 13 relative to handle 11. Handle 11 further includes a gripping surface 19 on the opposite side of actuator button 13 to facilitate grasping handle 11 with the fingers. Note that although an actuator in the form of a sliding button has been described in a preferred embodiment, various types of actuator mechanisms may be used to slide shaft 3 with respect to handle 11, including, for example, a plunger mechanism, a pair of scissor type handles, or a rotatable knob that converts rotational motion into axial motion. In addition, the actuator mechanism could be similar to that disclosed in commonly assigned, co-pending application Ser. No. 08/194,946, filed Feb. 14, 1994, which is incorporated herein by reference.

A tubular rod 21 extends through axial passage 9 of shaft 3 and axial bore 10 of handle 11 to support a wire 23 disposed through the center of rod 21. As shown in FIG. 2B, a disc 24 is fixed to the distal end of rod 21 and has a diameter larger than rod 21 and slightly less than axial passage 9 of shaft 3. Disc 24 ensures that rod 21 remains generally centered within shaft 3 during a surgical procedure. Wire 23 is fixed at its proximal end to handle 11, and is connected at its distal end to a clamp engaging means 25 having a pair of arms 27, 29 that extend through a slot 26 in disc 24 at the distal end of rod 21. Arms 27, 29 are rigid and, in an open position, oriented at an acute angle relative to the axial direction (as defined by axial passage 9) so that arms 27, 29 flare outward in the distal direction. Wire 23 could also be made rigid enough to extend through axial passage 9 of shaft 3 and axial bore 10 of handle 11 without support from rod 21.

Arms 27, 29 have distal tips 28, 30 that extend inwardly from arms 27, 29. Arms 27, 29 are biased radially outward to the open position shown in FIGS. 2B and 2D. Arms 27, 29 can be forced into a closed position (FIG. 2A) by axial movement of shaft 3, as described below. Distal tips 28, 30 of arms 27, 29 are generally perpendicular to the axial direction when arms 27, 29 are in the closed position so that engaging means 25 can hold onto clamp 2, as described below.

As shown in FIGS. 2A and 2B, button 13 can be moved along longitudinal slot 17 to slide shaft 3 in an axial direction with respect to handle 11 and rod 21. When shaft 3 is moved in a distal direction with respect to handle 11 and rod 21, arms 27, 29 are deflected inward by an inner wall 31 of axial passage 9 in shaft 3 (FIG. 2A). When shaft 3 is moved in a proximal direction with respect to handle 11 and rod 21, arms 27, 29 are released and allowed to open (FIG. 2B). It should be understood that the invention is not limited to the foregoing configuration. For example, rod 21 and engaging means 25 could be axially movable and shaft 3 fixed to handle 11, or both the engaging means and the shaft could be independently slidable with respect to the handle. However, the configuration shown in FIGS. 2A and 2B is presently preferred, since it maintains a constant distance between handle 11 and arms 17, 19 during actuation thereby maintaining clamp 2 a predetermined distance from the user's hand.

A knob 33 is fixed to the proximal end of rod 21 so that rod 21 can be rotated within handle 11 and shaft 3. Knob 33 includes a cylindrical extension 39 rotatably disposed within a cylindrical aperture 41 in handle 11. Extension 39 has a necked portion 43 having a smaller diameter than extension 39. A retaining ring 44, fixed to handle 11 by screws 45, rotatably retains necked portion 43 in aperture 41 of handle 11. Rotation of knob 33 will rotate rod 21 and arms 27, 29 about the longitudinal axis of shaft 3. Note that a variety of known mechanisms may be utilized for rotating arms 27, 29 relative to handle 11. Alternatively, arms 27, 29 may be rotated simply by turning handle 11 around its own axis.

Figure 3A:
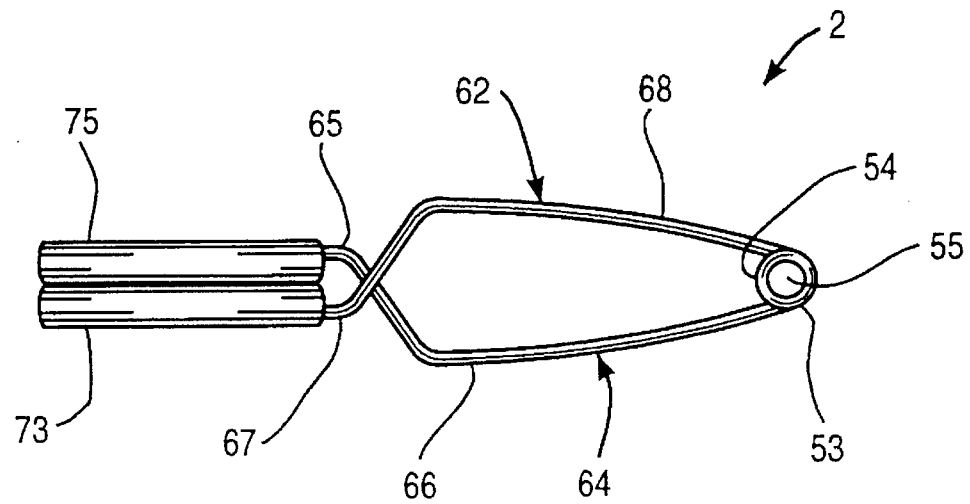
FIGS. 3A–3B are side and top views, respectively, of a clamp in the endoscopic clamping system of FIG. 1.
Figure 3B:
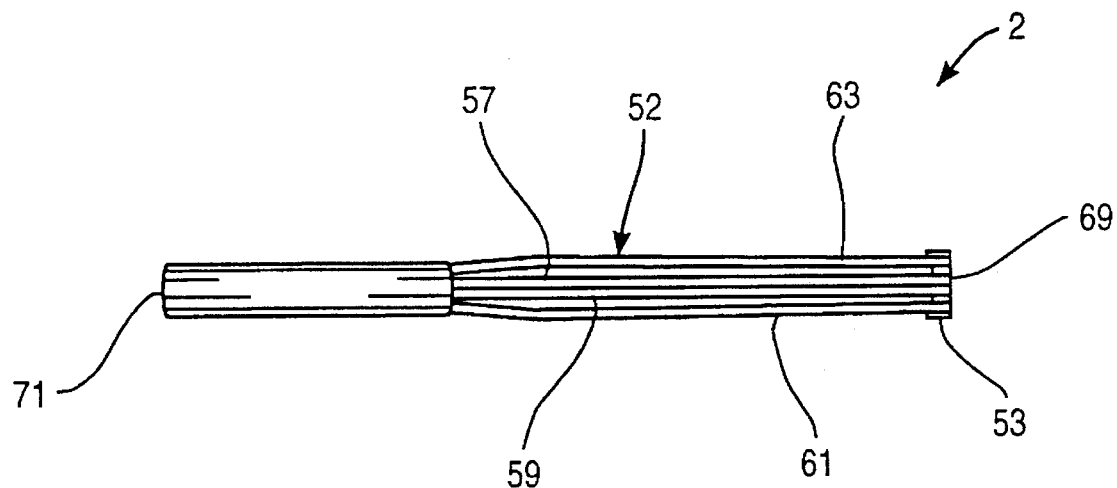

FIGS. 3A and 3B illustrate a preferred embodiment of clamp 2 according to the invention. Clamp 2 is preferably constructed of a single continuous length of wire 52 wrapped around a spool 53 to form coils 54 at the proximal end of clamp 2. Clamp 2 can also be constructed of two lengths of wire, one forming each jaw, riveted together at the proximal end. Spool 53 has a transverse bore 55 for releasably connecting clamp 2 to engaging means 25 of introducer 1 (discussed in more detail below). Alternatively, engaging means 25 could hold clamp 2 by direct contact with the curved proximal end of the wire, eliminating the need for spool 53.

Wire 52 forms two inner sections 57, 59 forming a first jaw 62 of clamp 2 and two outer sections 61, 63 forming a second jaw 64 of clamp 2. The outward surfaces of inner sections 57, 59 form a first camming surface 66 and the outward surfaces of outer sections 61, 63 form a second camming surface 68 along a proximal portion of clamp 2. Camming surfaces 66, 68 are adapted for sliding engagement with inner wall 31 of axial passage 9, as described below. Each set of wire sections 57, 59, 61, 63 cross over the longitudinal axis of clamp 2 to form first and second jaws 65, 67 at the distal portion of clamp 2.

Coils 54 of wire 52 are formed so as to create a spring force that biases jaws 65, 67 into the closed position, allowing clamp 2 to be released by introducer 1 and left clamped onto a tissue structure. This spring force is strong enough to allow clamp 2 to occlude vessels having high fluid pressure such as the mammary arteries. The blood in the mammary arteries typically has a fluid pressure between 70–100 mm Hg or more. Jaws 65, 67 of clamp 2 will preferably be maintained in the closed position under intraluminal fluid pressures of 70 to 150 mm Hg to ensure that blood and other fluids do not leak through the clamped portion of a mammary artery.

Camming surfaces 66, 68 provide a smooth, continuous surface oriented at an acute angle relative to the axial direction. Thus, sliding engagement of camming surfaces 66, 68 in the distal direction will force the proximal portions of clamp 2 together. Because the proximal and distal portions of each jaw am on opposing sides of the clamp axis, deflection of camming surfaces 66, 68 toward each other will move jaws 65, 67 away from each other.

It should be noted that the invention is not limited to the specific wire configuration shown in FIGS. 3A–3B. A variety of configurations are possible, so long as at least one camming surface is provided which is oriented at an angle relative to the axial direction so that axial sliding engagement with the camming surface will open and close the jaws. In addition, a variety of jaw configurations may be utilized on clamp 2 including Babcock, Kocher, Kelly, Allis, Glassman, DeBakey and Cooley-type jaws.

To avoid the possibility of damaging the vessel to which clamp 2 is applied, clamp 2 includes atraumatic means on at least the inner surfaces of jaws 65, 67. The atraumatic means preferably comprises two elastomeric sleeves 73, 75 wrapped around jaws 65, 67. Sleeves 73, 75 may have longitudinal grooves or other textural features (not shown) on opposing surfaces to facilitate gripping of the tissue structure. Sleeves 73, 75 can be constructed of any soft, elastomeric material such as rubber, foam material or surgical gauze, but are preferably made of silicone with a durometer within the range of 30 to 80 Shore A. Suitable sleeves are commercially available from Sil-Med Corp of Taunton, Mass. under the trade name "Vascular Paws".

The atraumatic means is not limited to the sleeves described above. For example, jaws 65, 67 could simply have soft pads bonded to their inner opposing surfaces. Alternatively, the wire could be configured so that jaws 65, 67 are separated by a predetermined distance (selected to minimize tissue damage) when in the closed position. This predetermined distance would depend on the size and resiliency of the particular tissue to be clamped and the fluid pressure within the vessel lumen.

Figure 4A:
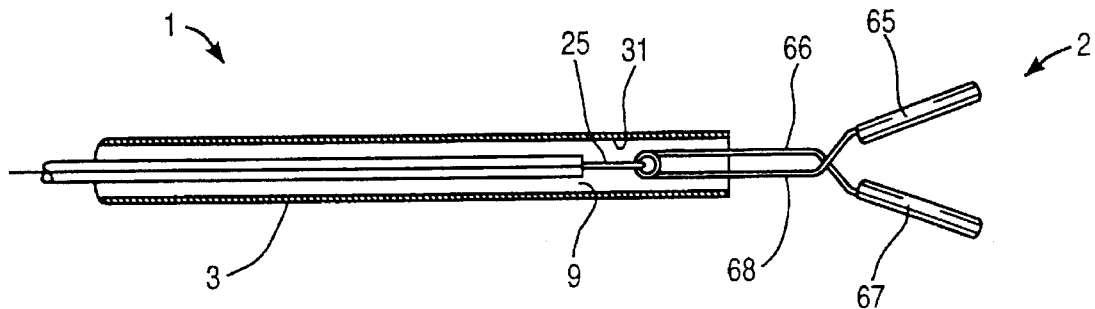
FIGS. 4A–4B are side cross-sectional views of a distal portion of the introducer and clamp of FIG. 1, illustrating the opening and closing of a pair of jaws on the clamp.
Figure 4B:
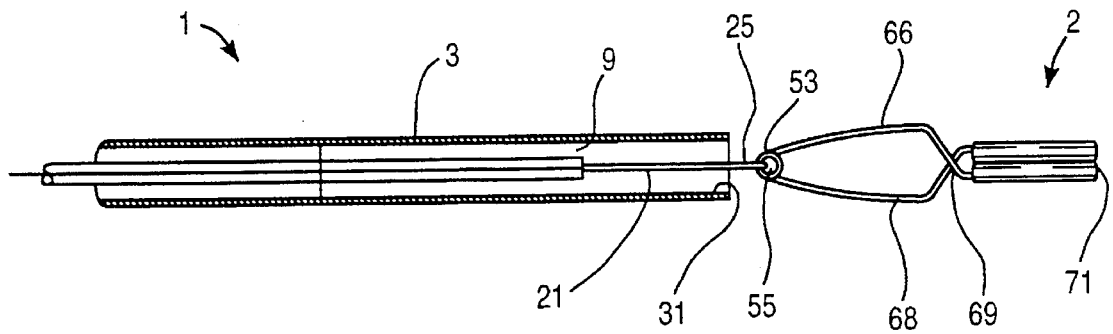

FIGS. 4A–4B illustrate the distal end of introducer 1 opening and closing jaws 65, 67 of clamp 2. Clamp 2 is connected to introducer 1 by arms 27, 29 which engage spool 53 of clamp 2. Arms 27, 29 have been closed by inner wall 31 of axial passage 9 so that distal tips 28, 30 of arms 27, 29 extend into transverse bore 55 to releasably hold clamp 2. When shaft 3 is moved distally towards clamp 2, inner wall 31 of axial passage 9 engages camming surfaces 66, 68 and forces the proximal portions of clamp 2 together, thereby opening jaws 65, 67 (FIG. 4A). To close jaws 65, 67, shaft 3 is moved in the proximal direction so that inner wall 31 of shaft 3 releases camming surfaces 66, 68 (FIG. 4B). Note that clamp 2 remains connected to introducer 1 during the opening and closing of jaws 65, 67. As discussed above, this facilitates repositioning clamp 2 after initial application to a vessel by simply reopening jaws 65, 67 without having to re-engage clamp 2 with introducer 1. Further movement of shaft 3 in the proximal directions opens arms 27, 29, releasing clamp 2 from introducer 1.

In the open position, jaws 65, 67 should be disposed sufficiently away from each other so that introducer 1 can easily position them around a tissue structure or blood vessel. Preferably, the distal ends of jaws 65, 67 are between 10–20 mm apart when in the open position. In the closed position, jaws 65, 67 are substantially parallel to each other to ensure that the blood vessel is uniformly and symmetrically clamped. In addition, jaws 65, 67 will preferably have a length from a proximal end 69 of clamp 2 to a distal end 71 between 15–25 mm to ensure that the entire blood vessel is clamped. Clamp 2 will have a cross-sectional profile small enough for introduction through a percutaneous penetration, preferably having a maximum transverse dimension between 4 and 10 mm.

Figure 5A:
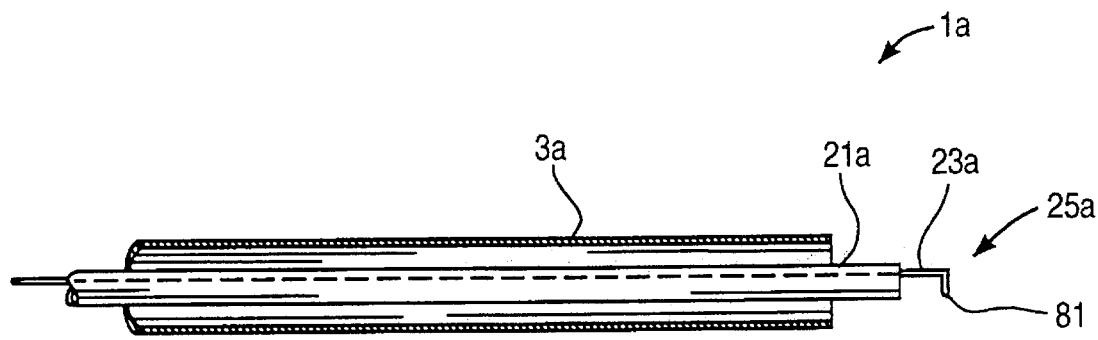
FIGS. 5A–5B are side cross-sectional views of a distal portion of a clamp introducer according to the invention showing two alternative embodiments thereof.
Figure 5B:
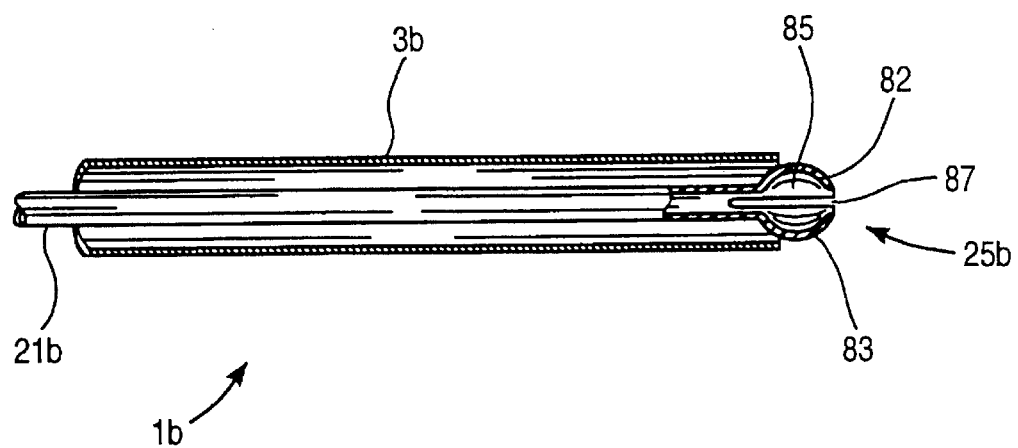

FIGS. 5A–5B show two alternative embodiments of clamp engaging means 25 of introducer 1 to releasably connect clamp 2 to introducer 1. Referring to FIG. 5A, introducer 1a has a clamp engaging means 25a comprising a wire 23a that extends beyond the distal end of a rod 21a. Wire 23a has a distal hook 81 configured to engage transverse bore 55 of clamp 2. Distal hook 81 of wire 23a is configured to be positioned within transverse bore 55 to hold clamp 2. Shaft 3a may then be translated distally relative to hook 81 to open the jaws of the clamp. To release clamp 2, distal hook 81 is withdrawn from transverse bore 55.

Referring to FIG. 5B, introducer 1b has a clamp engaging means 25b comprising a pair of jaws 82, 83 defining a socket 85 at the distal end of introducer 1b. Aperture 85 is configured to grasp a ball-shaped handle on the clamp, described below in reference to FIGS. 6A–6B. Jaws 82, 83 are separated by a slot 87 in the distal end of rod 21b and are biased radially outward so that axial movement of shaft 3b with respect to jaws 82, 83 opens and closes the jaws.

Figure 6A:
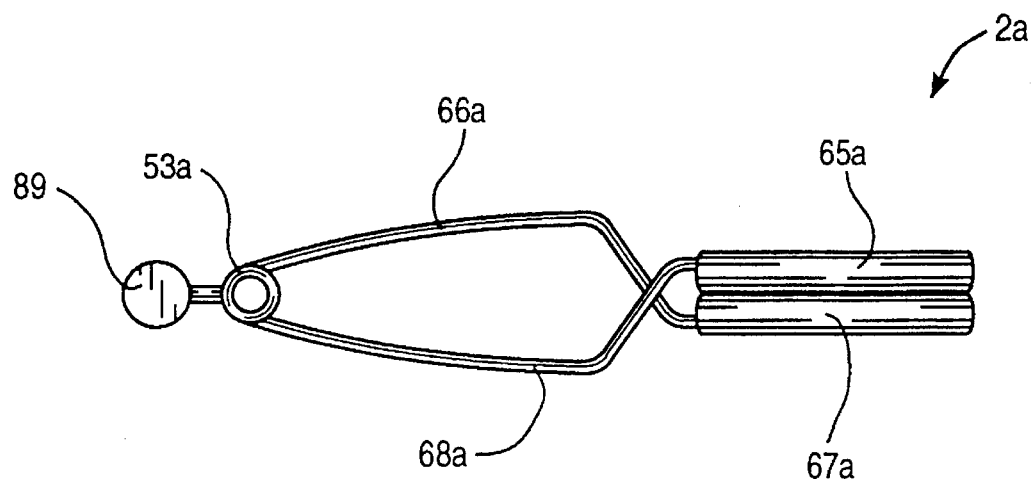
FIGS. 6A–6B are side views of two alternative embodiments of a clamp according to the invention for use with the introducer of FIG. 5B.
Figure 6B:
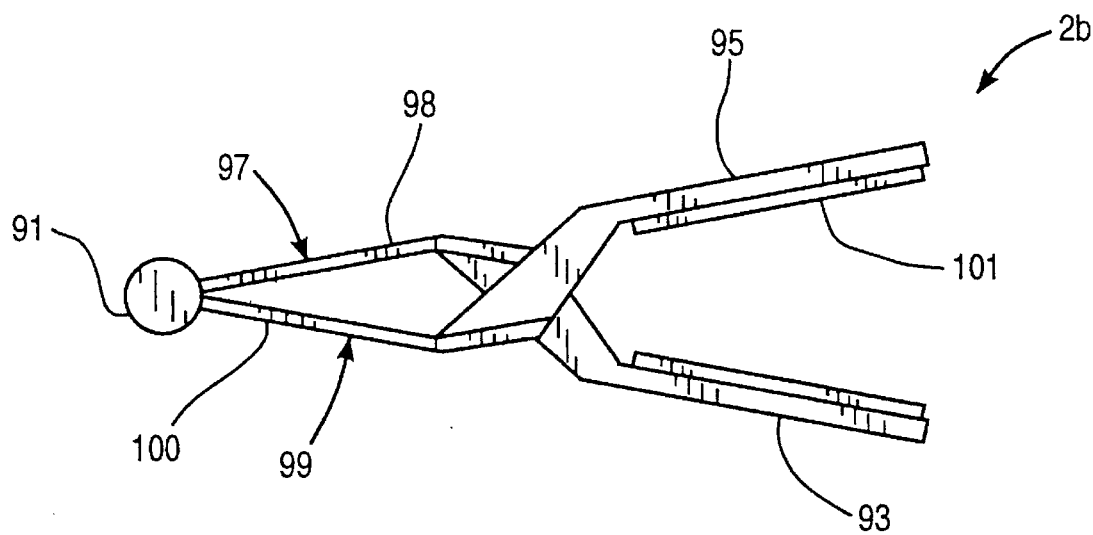

FIGS. 6A–6B show two alternative embodiments of clamp 2. Referring to FIG. 6A, a clamp 2a is similar to clump 2 of FIGS. 3A and 3B except for a ball-shaped handle 89 attached to the proximal end of spool 53a. Handle 89 serves to releasably connect clamp 2a to jaws 82, 83 at the distal end of introducer 1b, shown in FIG. 5B. Preferably, jaws 82, 83 will each have a generally hemispherical shape that is configured to receive a spherical handle on the clamp, as shown in FIGS. 6A and 5B. In this embodiment, the clamp can be re-engaged by the introducer from different angles because jaws 82, 83 can grasp handle 89 from many different directions. However, handle 89 and jaws 82, 83 can have a wide variety of shapes so long as jaws 82, 83 are configured to receive handle 89 at a single point of engagement.

Referring to FIG. 6B, a further embodiment of clamp 2 is shown. Clamp 2b comprises a spherical member or ball 91 at one end and first and second jaws 93, 95 at an opposite end. Ball 91 is coupled to jaws 93, 95 by arms 97, 99. Shaft 3 of introducer 1 slidingly engages camming surfaces 98, 100 on arms 97, 99 to open and close jaws 93, 95. Jaws 93, 95 each have pads 101 of a soft elastomeric material such as polyethylene foam to minimize damage to a tissue structure when the jaws are clamped onto the tissue structure. A suitable foam material is commercially available from 3M of St. Paul, Minn. under the brand name, "Foam Medical Tape".

A method of occluding an internal mammary artery in a coronary artery bypass grafting procedure according to the invention will now be described in conjunction with FIGS. 7–12. A more complete description of techniques for performing thoracoscopic coronary artery bypass procedures is found in co-pending application Ser. No. 08/023,778, which has been incorporated herein by reference. The patient undergoing the procedure is placed under general anesthesia and prepared in a conventional manner for cardiac surgery. At least one percutaneous intercostal penetration is made in the patient for introduction of introducer 1 and clamp 2. The terms "percutaneous intercostal penetration" and "intercostal penetration" as used herein refer to any penetration, in the form of a small cut, incision, hole or cannula, trocar sleeve or the like, through the chest wall between two adjacent ribs which does not require cutting, removing, or significantly displacing or retracting the ribs or sternum. Usually, the percutaneous penetration will require a puncture or incision of less than about 5 cm in length.

In a preferred embodiment, a plurality of access trocar sleeves will be positioned within an intercostal space in the left lateral chest of the patient, generally within the second, third, fourth, fifth, sixth or seventh intercostal spaces. The percutaneous intercostal penetration intended for introduction of introducer will preferably be in the third intercostal space. The trocar sleeves will generally be introduced between adjacent ribs and will penetrate the chest wall with their proximal end disposed just above the superior rib surfaces.

Although trocar sleeves are described as the preferred method of introducing instruments into the thoracic cavity, other similar methods may be employed. For example, introducer 1 can be introduced directly through a small percutaneous intercostal incision in the patient's chest. Trocar sleeves are preferred, however, to provide an open passage into the thoracic cavity and to protect adjacent tissue from injury.

Figure 7:
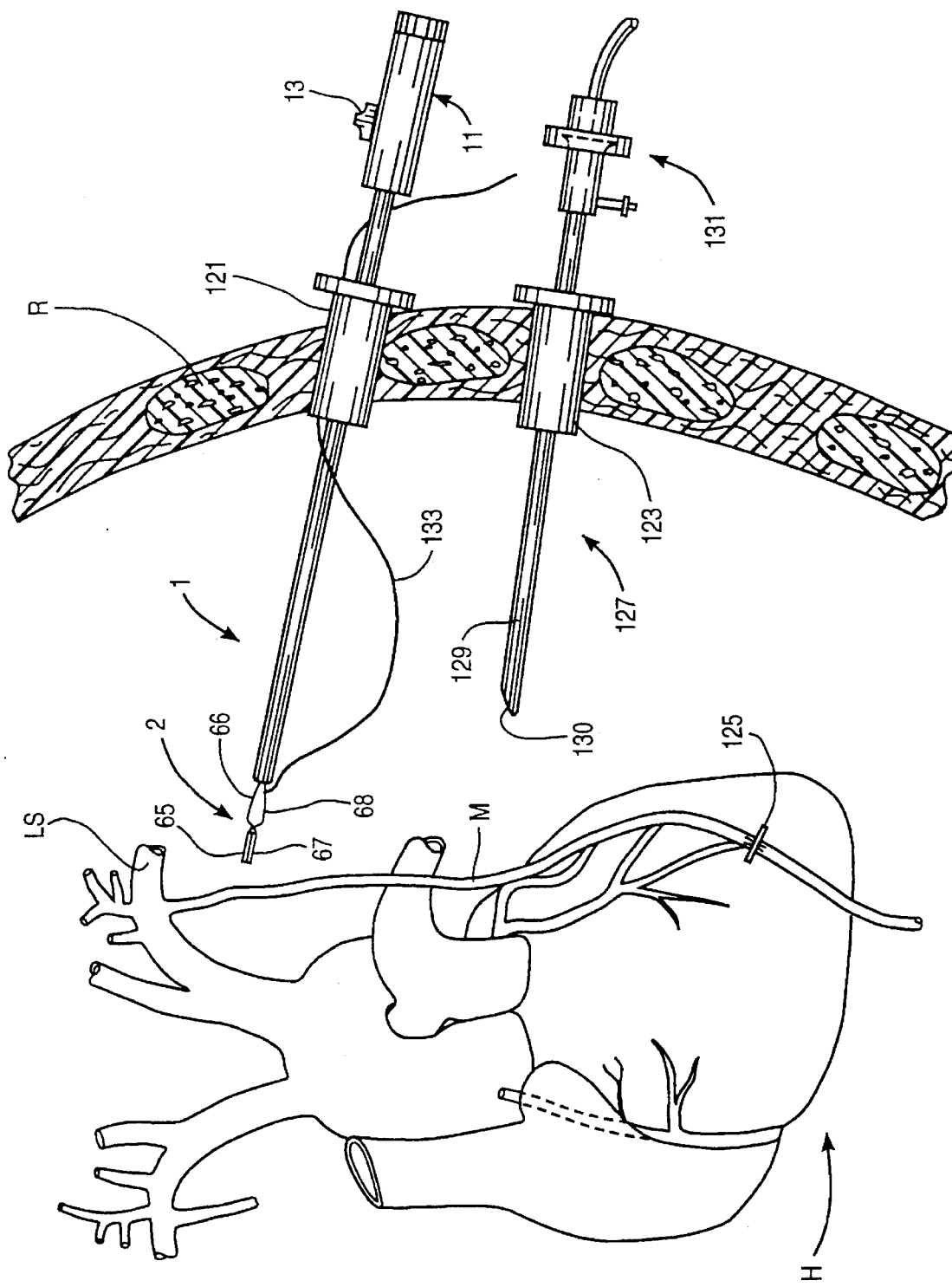
FIG. 7 is a schematic illustration showing the introducer of FIGS. 2A–2B introducing the clamp of FIGS. 3A–3B through a trocar sleeve in preparation for clamping onto a left internal mammary artery of a patient.

Two trocar sleeves 121, 123 are illustrated in FIG. 7. The trocar sleeves 121, 123 used for cardiac surgery will generally be shorter and will lack the gas sealing features of those used for conventional laparoscopic procedures. Typically, trocar sleeves useful for the present invention will have a length in the range from about 2–10 cm, and an internal diameter in the range from 2–15 mm, commonly known as thoracic trocars. Suitable trocar sleeves are available from United States Surgical Corp. of Norwalk, Conn., under the brand name "Thoracoport"™. In addition, the trocar sleeves can be flexible to permit manipulation of instruments introduced therethrough. Note that it will frequently be desirable to have additional trocar sleeves in position for the introduction of cutting and suturing instruments for performing the coronary artery bypass grafting procedure, as discussed in commonly assigned, co-pending application Ser. No. 08/023,778, now U.S. Pat. No. 5,452,733 which has been incorporated herein by reference.

The invention will now be described in reference to clamping the left internal mammary artery M in a coronary artery bypass grafting procedure. This artery is suitable as an arterial source for target locations on the left anterior descending coronary artery, the diagonal coronary artery, the circumflex/artery obtuse marginal artery, and the ramus intermedius coronary artery. The invention is also suitable for use on the right internal mammary artery. The right internal mammary artery is available for connection to all of the same target locations, as well as the right coronary artery and the posterior descending artery. The invention will further find use in clamping any of a variety of tubular vessels and other tissue structures which may require temporary clamping and/or retraction.

Before clamping and severing mammary artery M, the left lung will be collapsed to facilitate viewing of the operation. Known techniques for this procedure can be used, such as introducing a tube through the trachea into the left main stem bronchus and applying a vacuum through the tube to collapse the lung. After the lung is collapsed, a length of mammary artery M is dissected from the inner thoracic wall with a conventional electrosurgical instrument (not shown) introduced through trocar sleeve 121. A clip 125 is then applied downstream of the region of the mammary artery M that will be transected. Clip 125, which may be a conventional surgical clip, serves to permanently cut off the lower portion of mammary artery M downstream of clip 125 from the blood stream. Suitable clips can be obtained from Weck surgical instruments of Largo, Fla. under the brand name HEMOCLIP™. The heart H is then repositioned using suitable instruments introduced through trocar sleeves in order to better expose the coronary artery for the bypass operation.

As shown in FIG. 7, a viewing scope 127 is introduced through trocar sleeve 123 to a position suitable for viewing the target location on the mammary artery M. Viewing scope 127 can be a conventional laparoscope or thoracoscope, which typically consist of a rigid, elongated tube 129 containing a lens system and an eyepiece or camera mount 131 at the proximal end of the tube. A small video camera (not shown) is preferably attached to the camera mount and connected to a video monitor to provide a video image of the procedure. Preferably, the scope has a distal end 130 configured to allow lateral or angled viewing relative to tube 125. The viewing scope may also have a guidable tip that can be deflected or rotated by manipulating an actuator on a proximal end of tube 129. This type of scope is commercially available from Baxter Healthcare Corp. of Deerfield, Ill.

As an alternative to the above viewing systems, a visualization system for direct, stereoscopic visualization of the thoracic cavity could be utilized, as described in commonly assigned, co-pending application Ser. No. 08/135,387, filed Oct. 8, 1993, now abandoned or in co-pending application Ser. No. 08/227,366, filed Apr. 13, 1994, which are incorporated herein by reference. This visualization system comprises a surgical microscope coupled to an access cannula. The access cannula can be positioned percutaneously in an intercostal space, facilitating direct stereoscopic visualization through the access cannula into the chest cavity. This system provides high image quality and the natural hand-eye coordination of direct vision while allowing multiple persons to simultaneously view the surgical site.

To occlude mammary artery M, clamp 2, releasably coupled to arms 29, 31 of introducer 1, is introduced through trocar sleeve 121, as shown in FIG. 7. Clamp 2 is preferably introduced into the patient with jaws 65, 67 in the closed position to ensure that clamp 2 will pass easily through trocar sleeve 121. This also provides a smaller profile to avoid contact with other tissue structures in the patient's body. Clamp 2 is then moved near a target location on mammary artery M just below the junction of mammary artery M and the patient's left subclavian artery LS. Preferably, the target location will be between 2–10 cm from this junction. Occluding mammary artery M at this location keeps clamp 2 separated from the severing and grafting steps of the procedure, discussed below. A flexible tether 133, which may be conventional suture material, is connected to one of the proximal portions of clamp 2. Tether 133 extends through trocar sleeve 121 to maintain contact with clamp 2 when introducer 1 releases clamp 2 and is withdrawn from the patient. In the event clamp 2 becomes disengaged from introducer 1 and mammary artery M, it may be retrieved by pulling on tether 133. Moreover, if mammary artery M must be repositioned or otherwise manipulated after clamp 2 has been applied, tether 133 may be tensioned to apply traction to mammary artery M.

Figure 8:
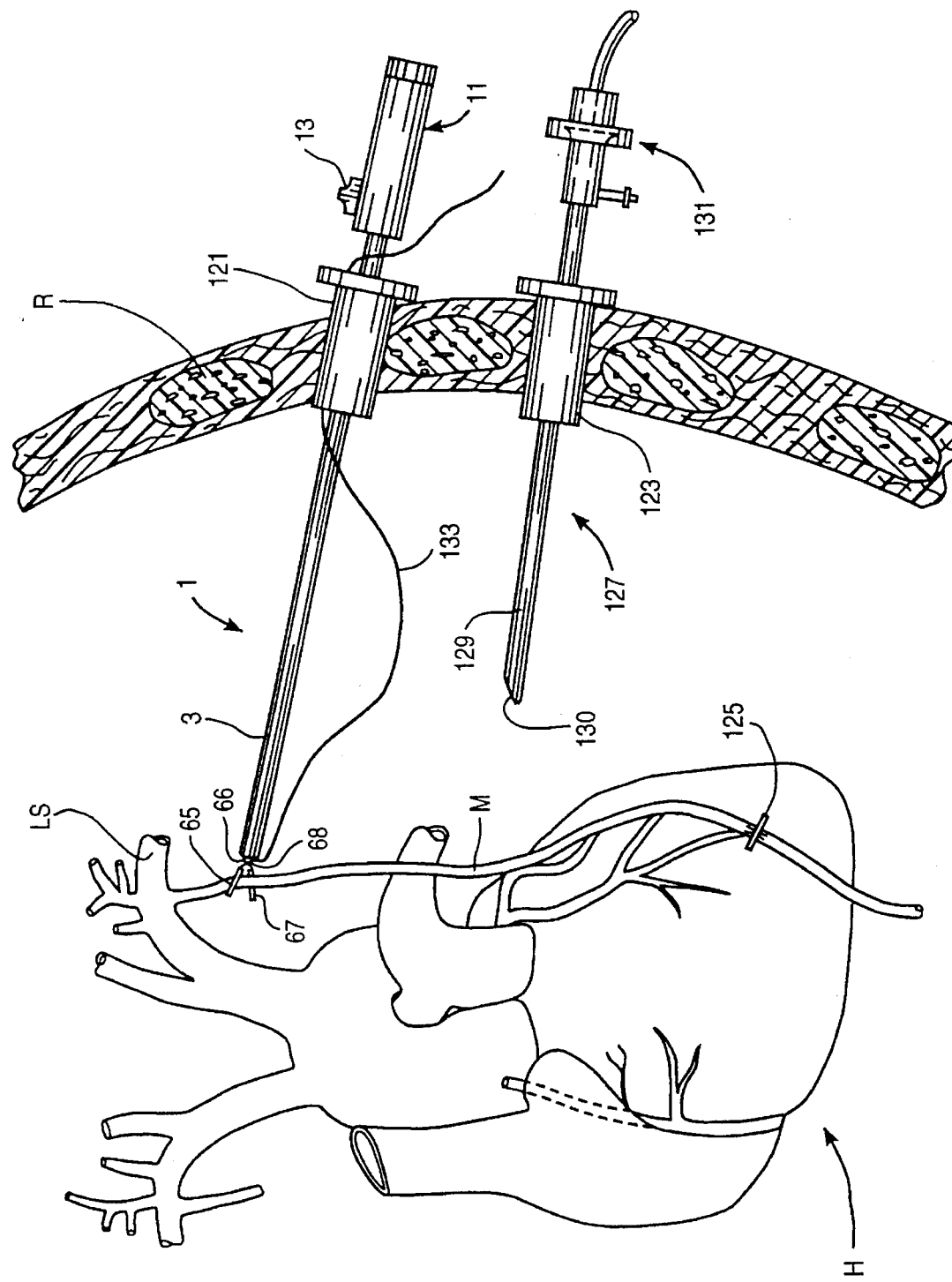
FIG. 8 illustrates the introducer positioning the open jaws of the clamp around the target location of the mammary artery.
Figure 9:
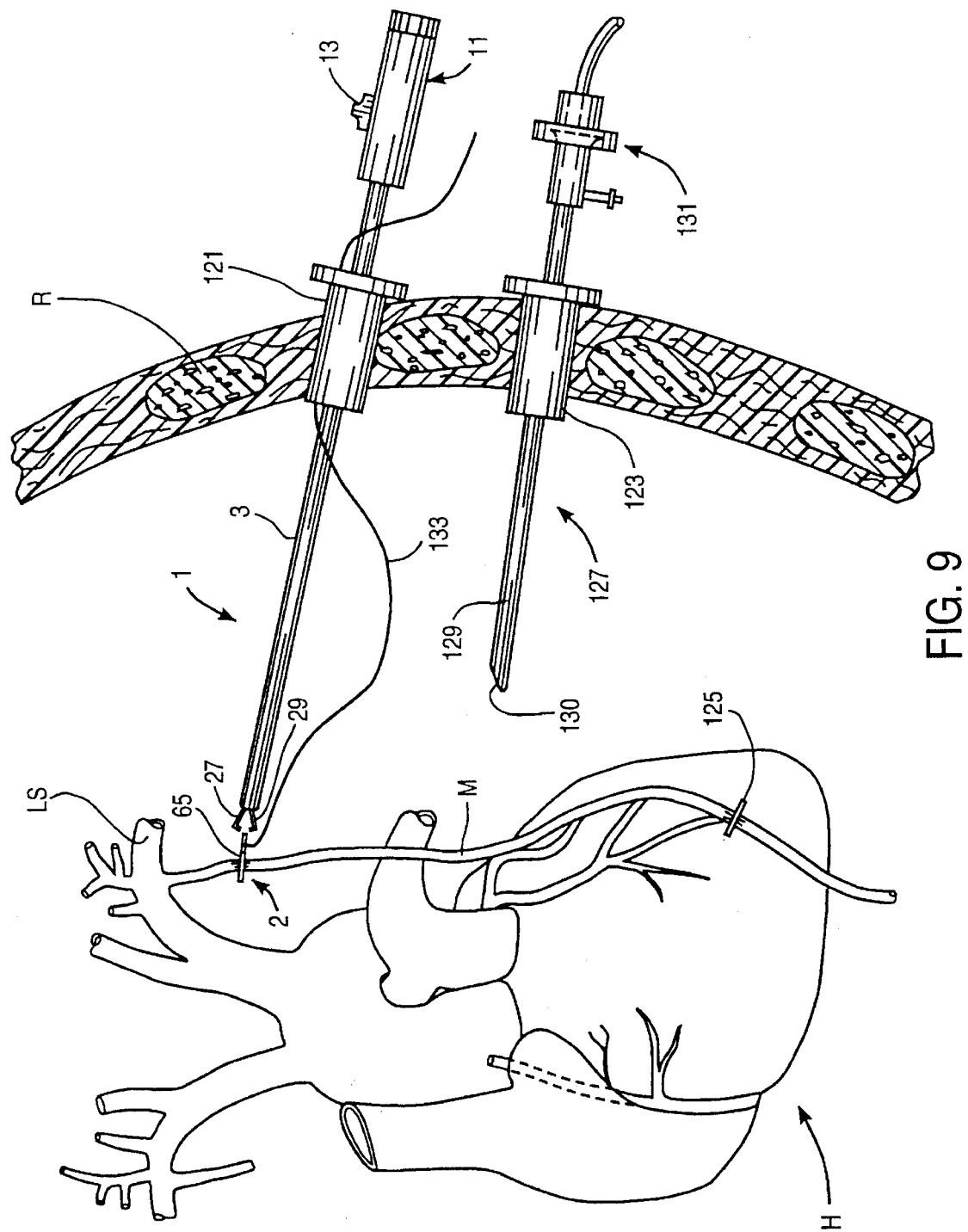
FIG. 9 illustrates the introducer after closing the jaws of the clamp onto the mammary artery and then releasing the clamp from the introducer.

Referring to FIG. 8, the surgeon now moves actuator button 13 in the distal direction to slidingly engage camming surfaces 66, 68 of clamp 2 with inner wall 31 of shaft 3. Camming surfaces 66, 68 move together and jaws 65, 67 move apart into the open position. The open jaws are then positioned around the target location of mammary artery M. If necessary, knob 33 can be rotated to orient clamp 2 at a suitable angle to clamp mammary artery M (FIG. 9 illustrates a 90 degree rotation from FIGS. 7 and 8). Once clamp 2 is in position, the surgeon moves actuator button 13 back in the proximal direction to release camming surfaces 66, 68, allowing jaws 65, 67 to close onto mammary artery M to occlude the lumen within the mammary artery. The surgeon can visually inspect the mammary artery M (or employ any other conventional means) to ensure that it is sufficiently occluded.

If mammary artery M is not completely occluded, the surgeon can easily reposition clamp 2. Actuator button 13 is moved in the distal direction to engage camming surfaces 66, 68 and open jaws 65, 67. The surgeon may then manipulate introducer 1 to move clamp 2 into a more effective position on mammary artery M. Actuator button 13 is then slid back in the proximal direction to release camming surfaces 66, 68 and close jaws 65, 67 onto mammary artery M.

Figure 10:
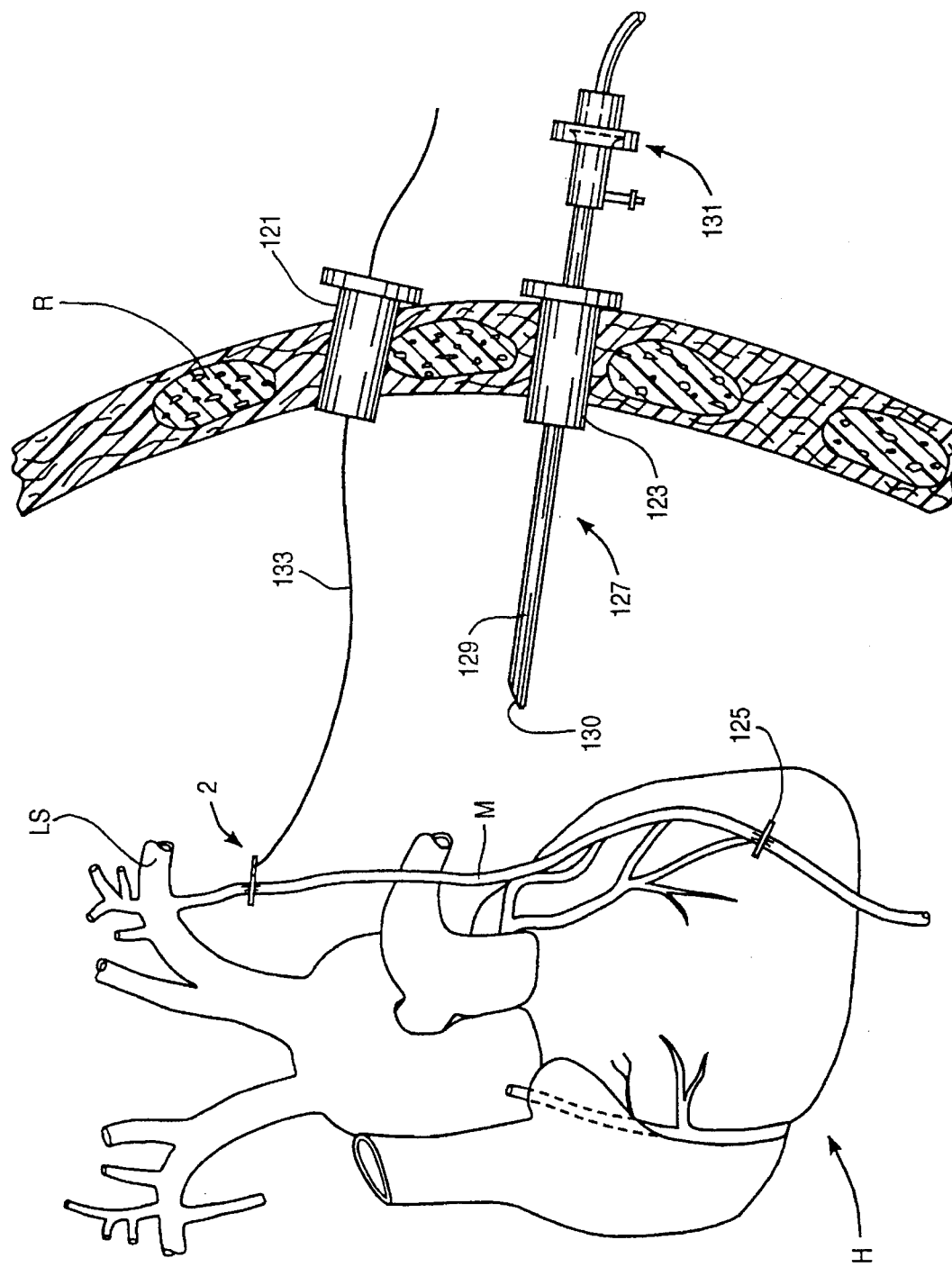
FIG. 10 illustrates the clamp applied to the mammary artery after the introducer has been removed from the patient.

Once the surgeon is satisfied that manunary artery M has been effectively occluded by clamp 2, the surgeon moves actuator button 13 further in the proximal direction to release arms 27, 29 of introducer 1 from bore 55 of clamp 2, as shown in FIG. 9. Introducer 1 can then be removed from the patient's body through trocar sleeve 121 to facilitate the surgeon's view during the rest of the operation. As shown in FIG. 10, clamp 2 remains attached to mammary artery M with tether 133 extending from clamp 2 to the exterior of the thoracic cavity. Note that if it is desirable, introducer 1 can remain in the patient's body and can even remain connected to clamp 2 to manipulate mammary artery M when needed.

After mammary artery M has been prepared and clamped, the heart will be arrested and the patient placed on cardiopulmonary bypass. It should be understood, however, that these steps could be performed before mammary artery M is transected. Arterial and venous cannulae are introduced into a femoral artery and a femoral vein, respectively, and connected to a cardiopulmonary bypass pump and. oxygenation system. The patient's aorta is then partitioned at a location between the brachiocephalic artery and the coronary ostia. Preferably, this partitioning is achieved by endovascularly advancing the distal end of a catheter to the desired location within the ascending aorta and expanding a balloon on the catheter to inhibit the flow of blood and other fluids past this location. The patient's heart will then be stopped, typically by introducing cardioplegic fluid into the coronary arteries through a lumen in the aortic occlusion catheter, with the patient's circulation maintained by cardiopulmonary bypass. This method for arresting the heart and establishing cardiopulmonary bypass is described in greater detail in commonly assigned, copending applications Ser. Nos. 07/991,188, filed Dec. 15, 1992, and 08/123,411, filed Sep. 17, 1993, now abandond, which are incorporated herein by reference.

Figure 11:
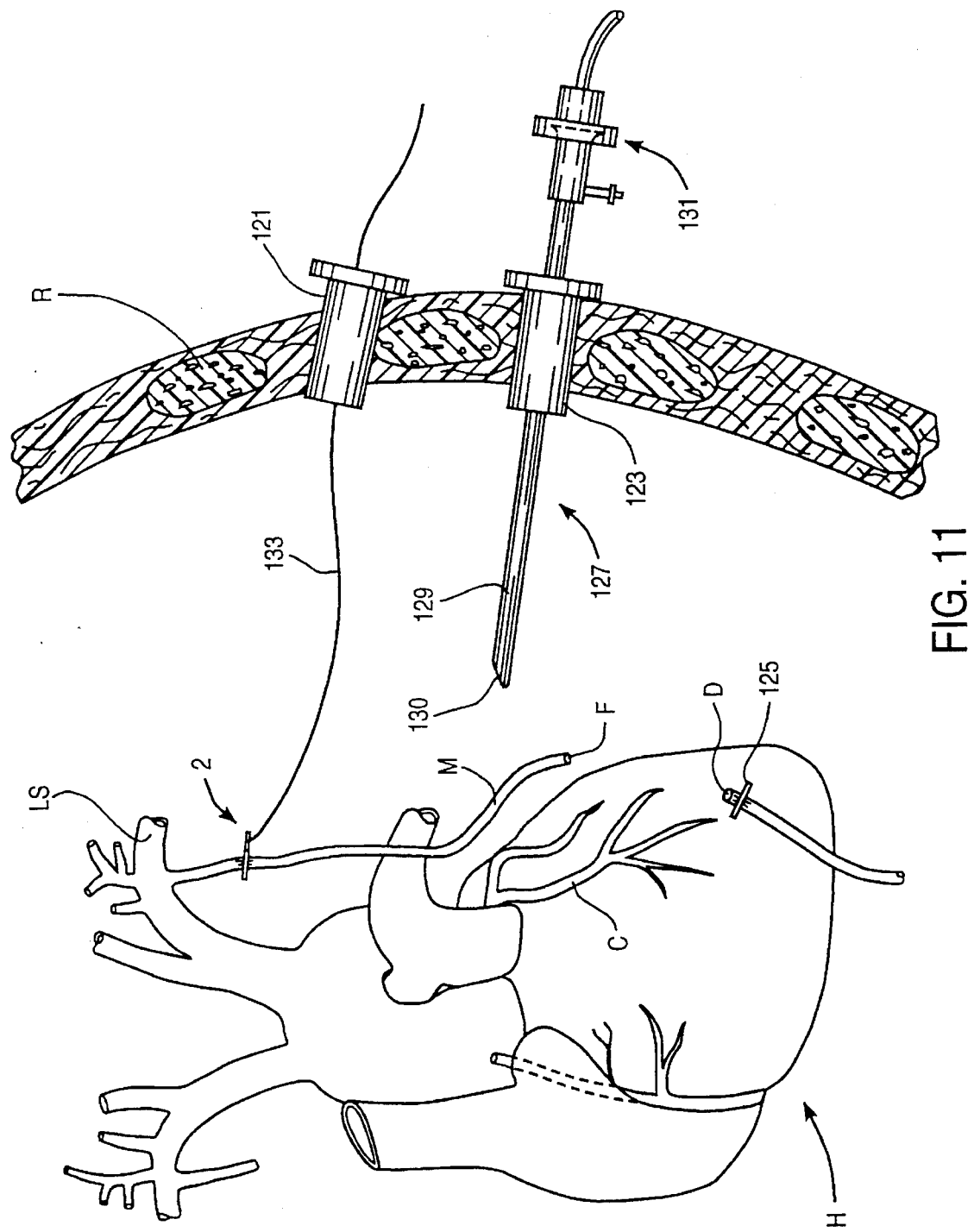
FIG. 11 illustrates the mammary artery after it has been ligated and divided at a location downstream of the clamp.
Figure 12:
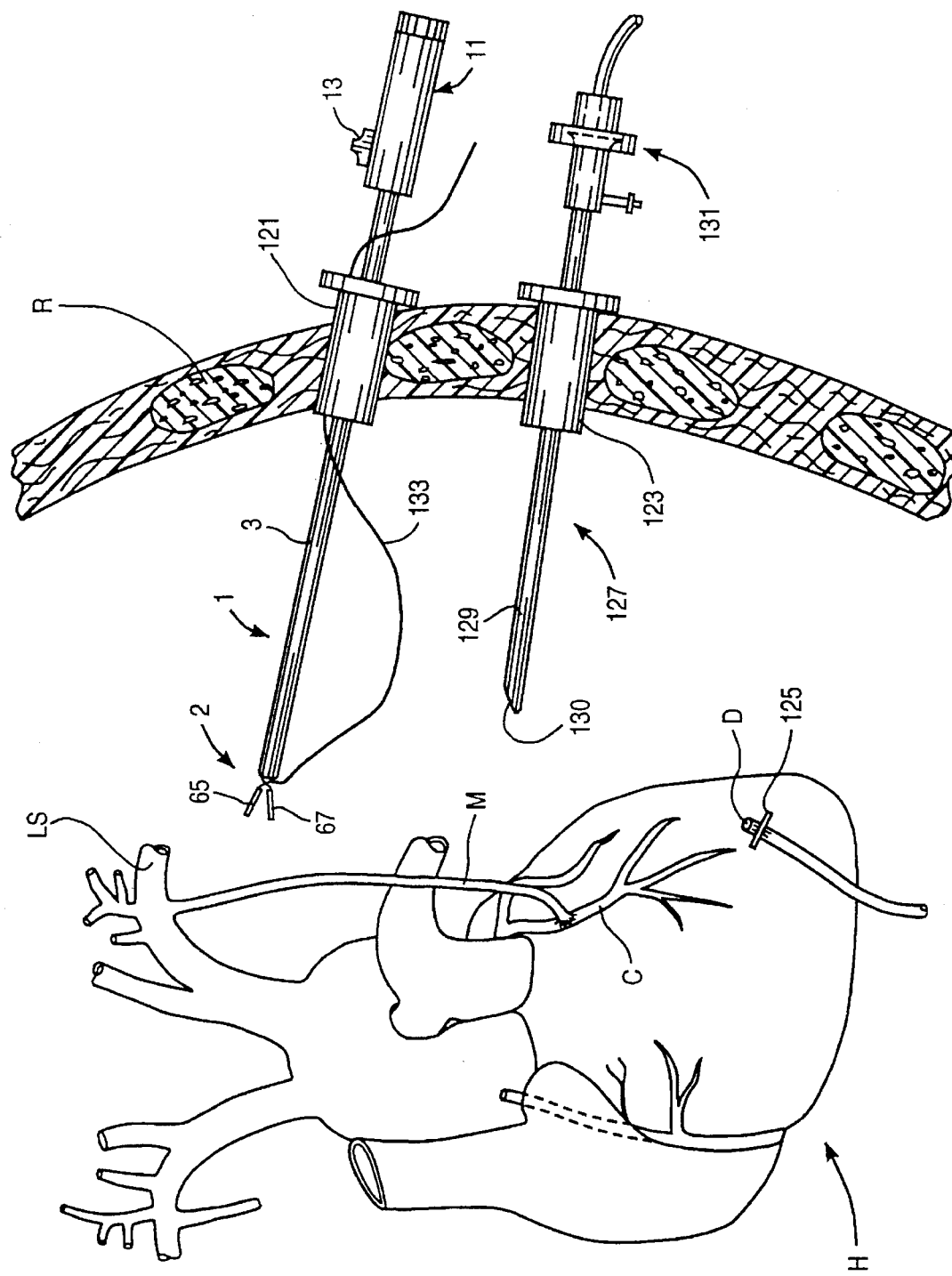
FIG. 12 illustrates the mammary artery attached to a coronary artery after completion of the coronary artery bypass grafting procedure, the introducer having released the clamp from the mammary artery to allow blood to flow through it.

FIGS. 11 and 12 illustrate the severing and grafting steps. Mammary artery M is ligated and divided at a location downstream of clamp 2 just above the subxyphoid with a conventional surgical cutting instrument (not shown) introduced through a trocar sleeve. Note that it will be desirable to cut the artery along a diagonal transverse line in order to provide an oval-shaped free end F. The free end F is then prepared for the anastomosis by conventional means. An incision (not illustrated) is then made in the wall of a coronary artery C downstream from an occluded or narrowed region therein. The incision is made with dimensions selected to match those of the free end F of mammary artery M. The free end F of mammary artery M is then joined to the coronary artery C around the incision by any of a variety of conventional techniques, including suturing, laser welding, microstapling, and the like. A preferred method of suturing is described in co-pending application Ser. No. 08/194,946, filed Feb. 11, 1994, now U.S. Pat. No. 5,501,698 which is incorporated herein by reference. Note that the clamp can be opened to release clamping pressure from the vessel to ascertain adequate flow in the mammary artery prior to connecting the free end to the coronary artery.

After mammary artery M has been grafted to the coronary artery C, introducer 1 is reintroduced through trocar sleeve 121. The surgeon engages clamp 2 with distal end 5 of introducer 1 and moves actuator button 13 in the distal direction to close arms 27, 29 around bore 55. Actuator button 13 is then moved further in the distal direction so that inner wall 31 of shaft 3 engages camming surfaces 66, 68 and opens jaws 65, 67. Blood and other fluids are now permitted to flow from mammary artery M into the coronary artery C thus bypassing the narrowed or occluded region in the coronary artery. Clamp 2 and introducer 1 can then be removed from the patient. The downstream free end D of mammary artery M will preferably remained clipped after the operation is complete. The patient's heart may then be restarted by discontinuing infusion of cardioplegic agents, and removing the aortic partitioning device from the ascending aorta. Percutaneous incisions and aortic punctures are closed, cardiopulmonary bypass is discontinued, and the patient is recovered from anesthesia.

It should be understood that the system and method of the present invention may also be used in conjunction with a conventional thoracotomy and open surgical techniques for coronary artery bypass grafting. However, the invention is particularly useful in the minimally-invasive procedures just described.

While the above is a complete description of the preferred embodiments of the invention, various alternatives, modifications and equivalents may be used. Therefore, the above description should not be taken as limiting the scope of the invention, which is defined by the appended claims.

What is claimed is:

1. A surgical clamp configured for introduction through a small percutaneous incision in the body for occluding a vessel in a body cavity, the surgical clamp comprising:

first and second jaws having distal sand proximal ends, the proximal ends being coupled together such that the distal ends are movable between an open position where the first and second jaws are disposed apart and a closed position where the first and second jaws are disposed closer together, the first and second jaws including atraumatic surfaces on the first and second jaws configured to atraumatically occlude the vessel without damaging the vessel;

means at the proximal ends of the first and second jaws for releasably holding the clamp, the holding means including a spherical member;

first and second camming surfaces on the first and second jaws distal to the holding means configured so that sliding engagement of the camming surfaces in an axial direction opens and closes the first and second jaws; and means for biasing the first and second jaws into the closed position.

2. The surgical clamp of claim 1 wherein the atraumatic surfaces comprise a soft, elastomeric material.

3. The surgical clamp of claim 1 wherein the holding means includes a transverse bore.

4. The surgical clamp of claim 3 wherein the transverse bore is a cylindrical bore encircled by a coil of wire.

5. The surgical clamp of claim 1 wherein the first and second jaws and the camming surfaces are formed from a single, continuous length of wire, the wire having a spring force that biases the first and second jaws into the closed position.

6. The surgical clamp of claim 5 wherein at least one of the camming surfaces is oriented at an angle with respect to an axial direction so that sliding engagement of the camming surfaces in the axial direction forces the proximal portion of the first and second jaws towards each other and opens the distal portions of the first and second jaws.

7. The surgical clamp of claim 1 wherein the first and second jaws have a distal portion for engaging the vessel and a proximal portion on which the camming surfaces are disposed, the proximal and distal portions being on opposing sides of the clamp so that deflection of the proximal portions toward each other moves the distal portions away from each other.

8. The surgical clip of claim 7 wherein the distal portion of the first and second jaws has an axial length between 15 and 25 mm.

9. The surgical clamp of claim 1 wherein the biasing means provides sufficient force to occlude a lumen of the vessel in which a fluid has a pressure of at least about 80 mm of mercury.

10. The surgical clamp of claim 9 wherein the biasing means comprises a torsion spring.

11. The surgical clamp of claim 1 wherein the first and second jaws are sized to occlude a lumen of a mammary artery.

12. The surgical clip of claim 1 wherein the distal ends of the first and second jaws are a distance apart when the first and second jaws are in the open position, the distance being between 10 and 20 mm.

13. A surgical clamp comprising:

a left wire member and a right wire member, said left wire member and said right wire member each comprising:

a first segment having a first camming surface on an outer surface thereof and a second segment having a second camming surface on an outer surface thereof, said first segment being deflectably connected to said second segment, a first crossover segment extending from a distal end of said first segment and a second crossover segment extending from a distal end of said second segment, said first crossover segment and said second crossover segment crossing over one another in slidable relation, a first jaw segment extending from said first crossover segment and a second jaw segment extending from said second crossover segment, said first jaw segment of said left wire member and said first jaw segment of said right wire member combining to form a first jaw of said surgical clamp, and said second jaw segment of said left wire member and said second jaw segment of said right wire member combining to form a second jaw of said surgical clamp, whereby when a mutually inward force is applied to said first camming surface and said second camming surface, said first jaw and said second jaw are spread apart, and when said mutually inward force is released, said first jaw and said second jaw move toward one another.

14. The surgical clamp of claim 13 wherein said left wire member and said right wire member are formed of a single, continuous strand of wire.

15. The surgical clamp of claim 13 further comprising a means for joining said left wire member and said right wire member.

16. The surgical clamp of claim 15 wherein said means for joining said left wire member and said right wire member comprises a first jaw surface connecting said first jaw segment of said left wire member to said first jaw segment of said right wire member and a second jaw surface connecting said second jaw segment of said left wire member to said second jaw segment of said right wire member.

17. The surgical clamp of claim 15 wherein said means for joining said left wire member and said right wire member comprises a first tubular member surrounding said first jaw segment of said left wire member and said first jaw segment of said right wire member and a second tubular member surrounding said second jaw segment of said left wire member and said second jaw segment of said right wire member.

18. The surgical clamp of claim 13 wherein, for each of said left wire member and said right wire member, said first segment is deflectably connected to said second segment at a common apex connecting a proximal end of said first segment to a proximal end of said second segment.

19. The surgical clamp of claim 18 further comprising a means for joining said apex of said left wire member to said apex of said right wire member.

20. The surgical clamp of claim 13 wherein, for each of said left wire member and said right wire member, said first segment is deflectably connected to said second segment by a torsional spring connecting a proximal end of said first segment to a proximal end of said second segment.

21. The surgical clamp of claim 20 wherein, for each of said left wire member and said right wire member, said torsional spring comprises a loop of wire of at least 360°.

22. The surgical clamp of claim 13 wherein said left wire member and said right wire member are mirror images of one another.

23. The surgical clamp of claim 13 wherein said second crossover segment of said left wire member and said second crossover segment of said right wire member are substantially parallel to one another and are spaced apart to form a gap therebetween, and wherein at least one of said first crossover segment of said left wire member or said first crossover segment of said right wire member pass through said gap, thereby maintaining an alignment between said first jaw and said second jaw of said clamp.

24. The surgical clamp of claim 13 wherein said second crossover segment of said left wire member and said second crossover segment of said right wire member are substantially parallel to one another and are spaced apart to form a gap therebetween, and wherein said first crossover segment of said left wire member and said first crossover segment of said right wire member pass through said gap, thereby maintaining an alignment between said first jaw and said second jaw of said clamp.

25. A method for occluding a mammary artery in a chest cavity defined by a plurality of ribs within a patient comprising:

introducing a surgical clamp releasably connected to an elongated shaft through a first percutaneous intercostal penetration between two ribs in the patient's chest;

viewing an internal portion of the patient's chest through a scope extending through a second percutaneous intercostal penetration between two ribs in the patient's chest;

applying the clamp to the mammary artery to occlude a lumen of the mammary artery; and releasing the clamp from the shaft.

26. The method of claim 25 wherein the elongated shaft is introduced through a cannula positioned in the percutaneous intercostal penetration.

27. The method of claim 25 wherein the percutaneous intercostal penetration is created in a left lateral portion of the patient's chest.

28. The method of claim 25 wherein the percutaneous intercostal penetration is in an intercostal space selected from the group consisting of the second intercostal space, the third intercostal space, the fourth intercostal space, the fifth intercostal space, the sixth intercostal space and the seventh intercostal space.

29. The method of claim 25 wherein the clamp is applied to a position along the mammary artery downstream from a subclavian artery a distance of about 1 to 5 cm.

30. The method of claim 29 further including the step of severing the mammary artery downstream of the position in which the clamp is applied to create a free end of the mammary artery.

31. The method of claim 30 further including the step of connecting the free end of the mammary artery to a coronary artery downstream from an occlusion in the coronary artery.

32. The method of claim 31 further including the step of removing the clamp from the mammary artery after the mammary artery has been connected to the coronary artery.

33. The method of claim 25 wherein the lumen of the mammary artery has a fluid pressure of at least 80 mm of mercury.

34. The method of claim 25 wherein the step of introducing the surgical clamp is performed without cutting, removing, or significantly displacing or retracting the ribs of the patient.

35. The method of claim 34 wherein the step of viewing an internal portion of the patient's chest through a scope is performed without cutting, removing, or significantly displacing or retracting the ribs of the patient.

36. A method for occluding a vessel in a chest cavity defined by a plurality of ribs within a patient comprising:

introducing a surgical clamp releasably held within an axial channel in an introducer through a percutaneous intercostal penetration between two ribs in the chest of the patient;

positioning first and second jaws of the clamp around the vessel;

sliding the clamp axially relative to the channel to extend the clamp distally therefrom thereby closing the jaws onto the vessel; and releasing the clamp front the introducer.

37. The method of claim 36 wherein the releasing step is performed after the sliding step so that the clamp is retained by the introducer after the jaws are closed onto the vessel.

38. The method of claim 36 wherein the introducer is introduced through a cannula positioned in a percutaneous penetration.

39. The method of claim 36 wherein the sliding step includes sliding a shaft of the introducer in a proximal direction with respect to the clamp to extend the clamp distally from an axial lumen in the shaft, the axial lumen having sidewalls for engaging camming surfaces on the clamp to open and close the jaws.

40. The method of claim 39 further comprising, before the positioning step, sliding the shaft in a distal direction with respect to the clamp, the sidewalls of the shaft engaging the camming surfaces on the clamp to open the jaws.

41. The method of claim 39 wherein the releasing step includes further moving the shaft in the proximal direction to open a clamp engaging means at a distal end of the shaft.

42. The method of claim 41 wherein the clamp engaging means comprises a pair of jaws defining an aperture for grasping a handle member on the clamp.

43. The method of claim 41 wherein the clamp engaging means comprises a pair of opposing arms for grasping a bore in the clamp.

44. The method of claim 39 wherein the releasing step includes disengaging a hook from a bore in the clamp.

45. The method of claim 36 further including the step of retracting the vessel by tensioning a flexible tether attached to the clamp.

46. The method of claim 36 further including, before the releasing step, the step of repositioning the vessel by manipulating the introducer after the jaws have closed onto the vessel.

47. The method of claim 36 wherein the step of introducing the surgical clamp is performed without cutting, removing, or significantly displacing or retracting the ribs of the patient.

48. The surgical clamp of claim 1 wherein the biasing means comprises a coiled wire torsion spring and wherein the holding means comprises a transverse bore through the coiled wire torsion spring.

* * * * *